United States Patent
Sekiya et al.

(10) Patent No.: US 7,401,779 B2
(45) Date of Patent: Jul. 22, 2008

(54) SHEET FEEDING APPARATUS

(75) Inventors: Takeshi Sekiya, Abiko (JP); Chikara Sato, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/001,040

(22) Filed: Dec. 2, 2004

(65) Prior Publication Data

US 2005/0127310 A1 Jun. 16, 2005

(30) Foreign Application Priority Data

Dec. 15, 2003 (JP) ............................. 2003-416623

(51) Int. Cl.
B65H 7/02 (2006.01)
(52) U.S. Cl. ................................. 271/265.01
(58) Field of Classification Search ............... 271/3.15, 271/3.16, 3.17, 4.02, 4.03, 10.02, 10.03, 271/110, 111, 227, 228, 258.01–263, 265.01–265.04, 271/152–156

See application file for complete search history.

(56) References Cited

U.S. PATENT DOCUMENTS

| | | | | |
|---|---|---|---|---|
| 4,428,041 A | * | 1/1984 | Honkawa | 700/78 |
| 4,571,055 A | * | 2/1986 | Nishiyama | 399/22 |
| 4,589,773 A | * | 5/1986 | Ido et al. | 356/623 |
| 4,608,704 A | * | 8/1986 | Sherman et al. | 377/8 |
| 4,670,647 A | * | 6/1987 | Hubble et al. | 250/214 AG |
| 4,703,172 A | * | 10/1987 | Sherman et al. | 250/223 R |
| 5,067,704 A | * | 11/1991 | Tsuihiji et al. | 271/262 |
| 5,220,177 A | * | 6/1993 | Harris | 250/548 |
| 5,250,803 A | * | 10/1993 | Christ et al. | 250/223 R |
| 5,850,582 A | | 12/1998 | Inoo et al. | 399/8 |
| 6,021,305 A | | 2/2000 | Sato et al. | 399/374 |
| 6,040,923 A | * | 3/2000 | Takashimizu et al. | 358/498 |
| 6,098,977 A | | 8/2000 | Sato et al. | 271/186 |
| 6,131,898 A | | 10/2000 | Hiroi et al. | 271/10.03 |
| 6,164,639 A | * | 12/2000 | Toh et al. | 271/171 |
| 6,203,003 B1 | | 3/2001 | Sato et al. | 271/3.01 |
| 6,219,503 B1 | | 4/2001 | Miyake et al. | 399/85 |
| 6,330,422 B1 | | 12/2001 | Sato et al. | 399/382 |
| 6,371,472 B1 | | 4/2002 | Miyake et al. | 270/58.14 |
| 6,386,080 B1 | | 5/2002 | Okamoto et al. | 83/73 |
| 6,481,705 B1 | * | 11/2002 | Okada | 271/4.03 |
| 6,493,113 B1 | | 12/2002 | Fujii et al. | 358/488 |
| 6,517,065 B2 | | 2/2003 | Miyake et al. | 270/58.09 |

(Continued)

FOREIGN PATENT DOCUMENTS

JP 2002-267767 9/2002

*Primary Examiner*—Patrick Mackey
*Assistant Examiner*—Jeremy Severson
(74) *Attorney, Agent, or Firm*—Fitzpatrick, Cella, Harper & Scinto (57) ABSTRACT

A sheet detecting apparatus provided with a light emitter and a light receiver for receiving light emitted from the light emitter through a sheet conveying path, wherein the light receiver detects any change in a quantity of light from the light emitter caused by a sheet passing on the conveying path intercepting the light emitted from the light emitter, to thereby detect the presence or absence of the sheet is provided with a V/I converting circuit for driving the light emitter, a comparing circuit for effecting negative feedback on the V/I converting circuit by an output signal, and changing the quantity of light of the light emitter, and a limiter circuit for applying a limitation to the negative feedback effected on the V/I converting circuit by the comparing circuit.

7 Claims, 7 Drawing Sheets

U.S. PATENT DOCUMENTS

| | | | |
|---|---|---|---|
| 6,577,512 B2 * | 6/2003 | Tripathi et al. | 363/21.17 |
| 6,603,951 B2 | 8/2003 | Sato et al. | 399/382 |
| 6,633,052 B2 * | 10/2003 | Walters et al. | 250/559.4 |
| 6,647,240 B2 * | 11/2003 | Fujii | 399/371 |
| 6,794,633 B2 * | 9/2004 | Iwasaki | 250/221 |
| 6,804,474 B2 * | 10/2004 | Morita et al. | 399/23 |
| 6,952,537 B2 * | 10/2005 | Fujii | 399/17 |
| 7,007,950 B2 * | 3/2006 | Im | 271/258.01 |
| 2001/0035603 A1 * | 11/2001 | Graves et al. | 271/265.01 |
| 2002/0190456 A1 | 12/2002 | Miyake et al. | 270/58.08 |
| 2003/0006549 A1 * | 1/2003 | Onishi et al. | 271/258.01 |
| 2003/0021608 A1 * | 1/2003 | Morita et al. | 399/23 |
| 2004/0245708 A1 * | 12/2004 | Takeuchi | 271/177 |

\* cited by examiner

| D/A OUTPUT | INITIAL LIGHT QUANTITY TRANSMISIBILITY ($\eta_0$) | THRESHOLD LIGHT QUANTITY TRANSMISSIBILITY ($\eta_{th}$) | DETERIORATED MARGIN (M) |
|---|---|---|---|
| 2.2V | 0.00009 | 0.000016 | 5.6 |
| 2.5V | 0.00009 | 0.000012 | 7.5 |
| 2.7V | 0.00009 | 0.00001 | 9.0 |
| 3.1V | 0.00009 | 0.0000075 | 12 |

SHEET FEEDING APPARATUS

BACKGROUND OF THE INVENTION

1. Field of the Invention

The invention relates to a sheet detecting apparatus for detecting the presence or absence of a sheet passing on a conveying path by a light emitter and a light receiver. The sheet detecting apparatus is utilized in an image forming apparatus such as a printer, an original conveying apparatus and a paper post-treating apparatus.

2. Related Background Art

Figure 9:
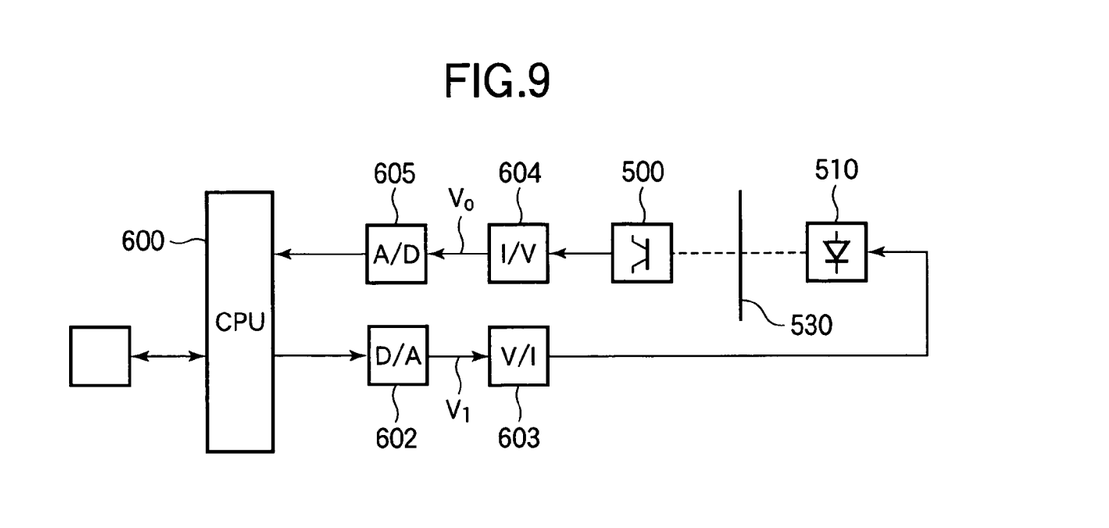
FIG. 9 is a block diagram of a conventional sheet detecting apparatus.

A conventional sheet detecting apparatus shown in FIG. 9 of the accompanying drawings, as described, for example, in Japanese Patent Application Laid-open No. 2002-267767, has been comprised of a light emitter 510 and a light receiver 500 disposed in opposed relationship with each other with a sheet conveying path 530 interposed therebetween, a CPU 600 for controlling the state of the sheet detecting apparatus, a D/A converter 602 for converting a control signal from the CPU 600 into an analog signal, a voltage-current converting circuit (V/I converting circuit) 603 for converting an output from the D/A converter 602 into a current and generating a driving current for causing the light emitter 510 to emit light, a current-voltage converting circuit (I/V converting circuit) 604 for converting a photoelectric current generated by the light receiver into a voltage, and an A/D converter 605 for converting an output voltage from the I/V converting circuit into a digital signal and transmitting it to the CPU 600.

Such a conventional sheet detecting apparatus has detected the presence or absence of a sheet by the sheet intercepting light between the light emitter 510 and the light receiver 500 disposed in opposed relationship with each other as described in Japanese Patent Application Laid-open No. 2002-267767.

In the above-described conventional sheet detecting apparatus, however, there has been the problem that when dust such as paper powder adheres to the light emitter and the light receiver and an output value from the light receiver decreases, it is wrongly recognized that the sheet has passed, in spite of the sheet having not passed. If in this case, the sensitivity of the sheet detecting apparatus is set high in order to prevent the wrong recognition, there has arisen the problem that when a thin sheet is passed, light is transmitted therethrough and the sheet cannot be detected.

Also, there has been proposed a sheet detecting apparatus provided with an automatic correcting method of taking out and storing an output signal from a light receiver as the data of an initial state, comparing it with an output signal from the light receiver periodically measured, and adjusting the quantity of light of a light emitter in conformity with the comparison signal to thereby maintain it in an optimum state.

In such a sheet detecting apparatus however, it has been difficult to set the timing for monitoring the output signal from the light receiver, and this has led to the undesirable possibility that for example, automatic correction cannot be appropriately effected for such an unexpected cause as a sudden change in temperature or the temporary adherence of dust. Also, there has been the problem that the power supply to the sheet detecting apparatus is cut off during the renewal of correction data and the correction data so far backed up is destroyed.

SUMMARY OF THE INVENTION

It is an object of the present invention to solve the above-noted problems peculiar to the conventional sheet detecting apparatuses, and to provide a sheet detecting apparatus in which the quantity of emitted light from a light emitter is automatically corrected so that the quantity of light from a light receiver may become optimum for detecting a sheet passing on a conveying path to thereby prevent wrong detection. Further, it is an object of the present invention to provide a sheet detecting apparatus which can make automatic correction follow even such an unexpected cause as a sudden change in temperature or the temporary adherence of dust to thereby effect detection appropriately and prevent wrong detection.

In order to achieve the above objects, according to the present invention, a sheet detecting apparatus provided with a light emitter and a light receiver for receiving light emitted from the light emitter through a sheet conveying path, wherein the light receiver detects any change in the quantity of light from the light emitter caused by a sheet passing on the sheet conveying path intercepting the light emitted from the light emitter to thereby detect the presence or absence of the sheet is provided with a driver for driving the light emitter, a comparing circuit for effecting negative feedback on the driver by an output signal from the light receiver to thereby change the quantity of light of the light emitter, and limiter for applying a limitation to the amount of feedback effected on the driver by the comparing circuit.

The light emitter and the light receiver may be disposed so as to be opposed to each other with the conveying path interposed therebetween. Also, the light emitter and the light receiver may be disposed on one sheet surface side of the conveying path, and a light guiding member such a prism or an optical rod for guiding the light from the light emitter to the light receiver may be provided on the opposite side of the conveying path.

According to the present invention, the negative feedback is directly effected on the driver by the comparing circuit based on the output signal from the light receiver and therefore, even if for example, the output value from the light receiver decreases, such automatic correction as will adjust the quantity of light of the light emitter so as to be increased, to thereby being about an optimum state for detecting the sheet passing on the conveying path is always effected. Also, since the automatic correction is always effected, the automatic correction can follow even a sudden change or the like in a measuring environment.

The comparing circuit may preferably effect the negative feedback on the driver so that the quantity of light from the light emitter received by the light receiver when the sheet is not passing on the sheet conveying path may maintain an allowable quantity of received light.

The optical path from the light emitter to the light receiver may preferably be astride the sheet conveying path at a plurality of locations.

The light emitter and the light receiver may preferably be disposed on one sheet surface side of the sheet conveying path, and the light guiding member for guiding the light from the light emitter to the light receiver may preferably be disposed on the other sheet surface side of the sheet conveying path.

Other objects and features of the present invention will become apparent from the following description and the accompanying drawings.

DESCRIPTION OF THE PREFERRED EMBODIMENTS

A preferred embodiment of this invention will hereinafter be described in detail by way of example with reference to the drawings. However, the dimensions, materials, shapes, relative arrangement, etc. of constituent parts described in this embodiment, unless specifically described, are not intended to restrict the scope of this invention thereto.

Figure 1:
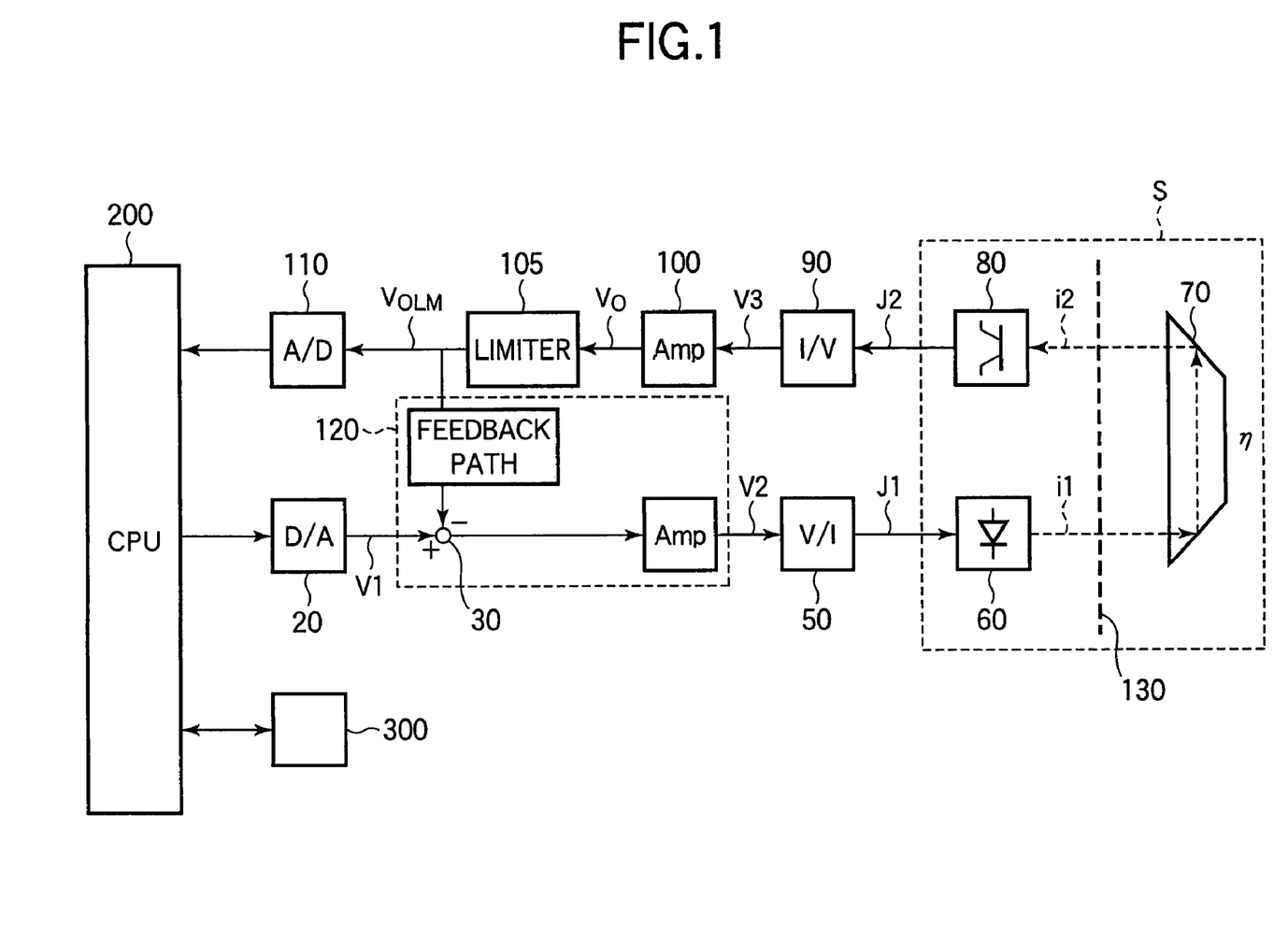
FIG. 1 is a block diagram of a sheet detecting apparatus according to an embodiment of the present invention.

FIG. 1 is a bock diagram of a sheet detecting apparatus according to an embodiment of the present invention.

The sheet detecting apparatus according to the present embodiment is provided with a light emitter 60 such as an LED and a light receiver 80 such as a phototransistor disposed on one sheet surface side of a sheet conveying path 130, and a light guiding member 70 disposed on the other sheet surface side of the sheet conveying path 130 for guiding light from the light emitter 60 to the light receiver 80 by reflections.

Also, the sheet detecting apparatus is provided with a CPU 200 for controlling the state of the sheet detecting apparatus, a D/A converter 20 for converting a control signal from the CPU 200 into an analog signal, a voltage-current converting circuit (hereinafter referred to as the V/I converting circuit) 50 which is a driver for converting an output from the D/A converter 20 into a current and generating a driving current for causing the light emitter 60 to emit light, a current-voltage converting circuit (hereinafter referred to as the I/V converting circuit) 90 for converting a photoelectric current generated by the light receiver 80 into a voltage, an amplifying circuit 100 for amplifying an output voltage from the I/V converting circuit 90, a limiter circuit 105 for clamping an output voltage from the amplifying circuit 100 by a predetermined voltage and limiting the output voltage, a comparing circuit 120 for comparing a predetermined reference voltage outputted from the D/A converter 20 with the output voltage of the limiter circuit 105, amplifying the differential voltage and applying negative feedback to the V/I converting circuit 50, and an A/D converter 110 for converting an output voltage from the limiter circuit 105 into a digital signal and transmitting it to the CPU 200.

Also, a non-volatile memory (EEPROM) 300 stores therein the set value of the D/A converter 20 and the initial value of the output of the A/D converter 110.

Figure 2:
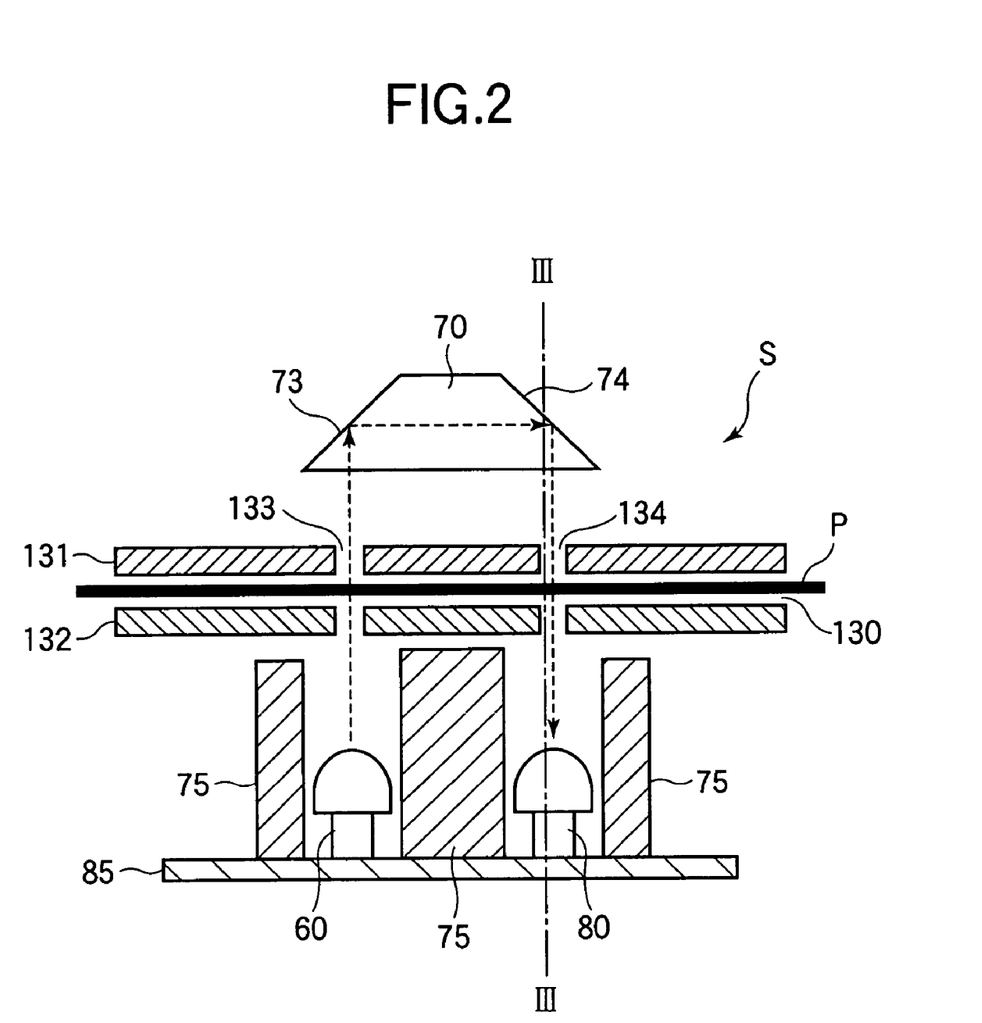
FIG. 2 shows the disposition of the sensor portion S of the sheet detecting apparatus according to the present embodiment.

FIG. 2 shows the disposition of the sensor portion S of the sheet detecting apparatus according to the present embodiment.

In FIG. 2, the sensor portion S is constituted by the light emitter 60, the light receiver 80 and the light guiding member 70. The light emitter 60 and the light receiver 80 are mounted on a printed substrate 85. A sensor hood 75 projected from the printed substrate positions the light emitter 60 and the light receiver 80 at predetermined positions and also, prevents light from the other portion than the light emitter 60 from being received as noise by the light receiver 80. Further, the sensor hood 75 prevents cross talk between the light guiding member 70 and the light receiver 80.

Conveying guides 131 and 132 are disposed in opposed relationship with each other with a predetermined interval therebetween, and a conveying path 130 for a sheet P is formed therebetween. Also, the conveying guides 131 and 132 are formed with a first slit 133 and a second slit 134 at equidistant positions in the conveying direction of the sheet P with a predetermined interval therebetween.

The light guiding member 70 is a prism having reflecting surfaces 73 and 74, and the light outputted from the light emitter 60 passes through the first silt 133 and enters the light guiding member 70, and is reflected by the reflecting surface 73 and passes through the light guiding member 70, and is again reflected by the reflecting surface 74 and passes through the second sit 134, and enters the light receiver 80.

In FIG. 2, the sheet conveyed on the conveying path 130 passes from the upper portion of the plane of the drawing sheet to the inner part of the plane of the drawing sheet, and intercepts the light between the light emitter 60 and the light guiding member 70 and the light between the light guiding member 70 and the light receiver 80 at a time.

Figure 3:
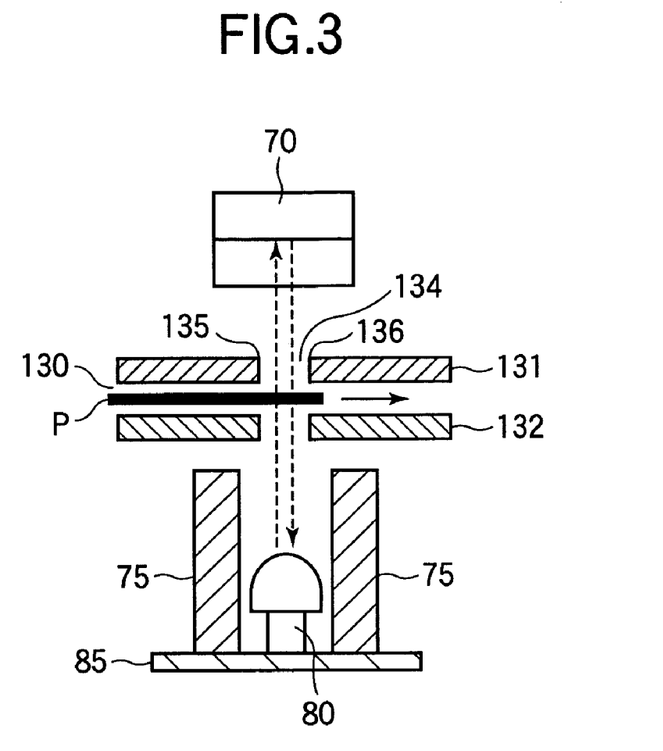
FIG. 3 is a cross-sectional view of the sheet detecting apparatus according to the present embodiment taken along the line III-III of FIG. 2.

FIG. 3 is a cross-sectional view taken along the line III-III of FIG. 2. The sheet P travels from the left toward the right on the conveying path 130. The second slit 134 is defined by edges 135 and 136 in the sheet conveying direction. The leading edge of the sheet P passes through the second silt 134 in the order of the edge 135 and the edge 136.

Figure 4:
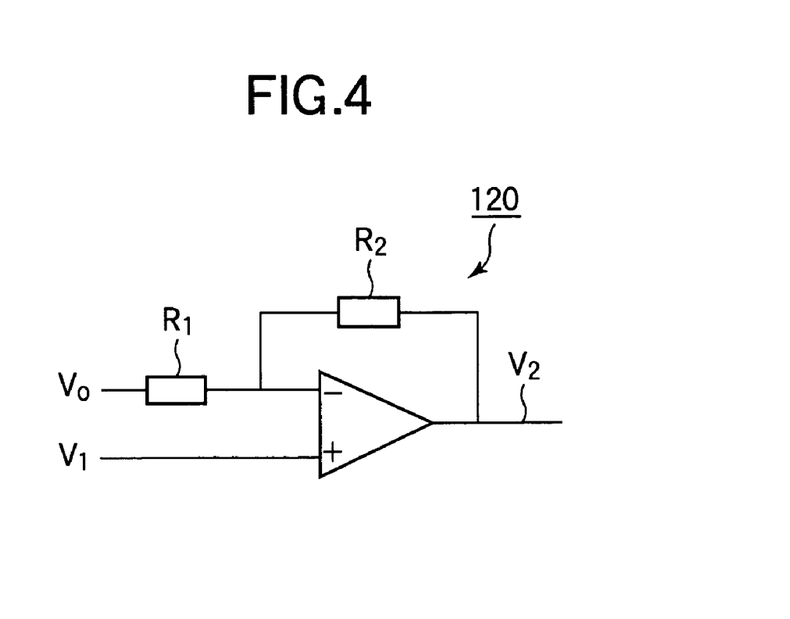
FIG. 4 shows the construction of a comparing circuit (differential amplifying circuit).

The comparing circuit 120 is a differential amplifying circuit having two inputs, and the specific construction thereof is shown in FIG. 4. The comparing circuit 120 amplifies $V_2$ outputted by the use of a predetermined reference voltage $V_1$ outputted from the D/A converter 20 and an output voltage $V_0$ from the I/V converting circuit 90, and is provided with resistors $R_1$ and $R_2$. The output voltage from the I/V converting circuit 90 becomes $V_0$ when the limiter circuit 105 does not operate, but becomes $V_{OLM}$ when the limiter circuit 105 has operated. Here, the value of $V_{OLM}$ can be arbitrarily set by the allowed voltage of the compring circuit 120 and the constructions of the other circuits. It is also possible to utilize the output saturation of the amplifying circuit 100 as the limiter circuit 105. In the following, $V_{OLM}$ is handled as $V_0$ unless particularly indicated.

In this case, the gain of the comparing circuit becomes $G_1 = R_2/R_1$. Accordingly, the output voltage of the comparing circuit becomes $$V_2 = (1+G_1)V_1 - G_1 \times V_0 \quad \text{(expression 1).}$$

According to the thus constructed sheet detecting apparatus according to the present embodiment, when the sheet is not conveyed to the conveying path 130, the light emitted from the LED which is the light emitter 60 is guided to the phototransistor which is the light receiver 80 by the light guiding member 70, and the light receiver 80 outputs a current conforming to the quantity of received light. The output current from the light receiver 80 is converted into a voltage by the I/V converting circuit 90, and is suitably amplified by the amplifying circuit 100. Then, the output voltage from the amplifying circuit 100 is directly negatively fed back to the comparing circuit 120 via the limiter circuit 105. Then, the comparing circuit 120 compares and amplifies the output voltage from the amplifying circuit 100 in conformity with a control signal from the CPU 200 with the reference voltage $V_1$ outputted from the D/A converter 20 as the reference, and outputs it to the V/I converting circuit 50.

Therefore, when the output voltage from the light receiver 80 does not differ from the output voltage in an initial state, the output voltage from the comparing circuit 120 is not amplified, but yet if the output voltage from the light receiver 80 drops, the comparing circuit 120 suitably amplifies the output voltage in the comparison with the reference voltage, and the quantity of emitted light of the light emitter 60 is always automatically corrected so that the sensor portion S may assume an optimum state for detecting the sheet passing on the conveying path.

While in the above-described embodiment, there has been shown an example in which the output voltage $V_1$ obtained by the output signal from the CPU 200 being converted by the D/A converter 20 is used as the reference voltage, design may be made such that without resort to the output signal from the CPU 200, a predetermined reference voltage is generated by a power supply provided independently of the CPU.

Here, when the transmission function of the V/I converting circuit 50 is defined as $G_2$, and the conversion efficiency of the light emitter 60 is defined as $G_3$, and the light quantity transmissibility from the light emitter 60 to the light receiver 80 is defined as $\eta$, the input light quantity i2 to the light receiver 80 is $$i2 = V_2 \times G_2 \times G_3 \times \eta \quad \text{(expression 2)}.$$

Also, the conversion efficiency of the phototransistor which is the light receiver 80 is defined as $G_4$, the transmission function of the I/V converting circuit 90 is defined as $G_5$, and the transmission function of the amplifying circuit 100 is defined as $G_6$, and the output voltage $V_{OLM}$ from the limiter circuit 105 when the limiter circuit 105 is not operating becomes equal to the output voltage $V_0$ of the amplifying circuit 100 and therefore, $V_{OLM}$ is $$V_{OLM} = V_0 = G_4 \times G_5 \times G_6 \times i2 \quad \text{(expression 3)}.$$

Accordingly, from the above-mentioned expression (1), expression (2) and expression (3), the output voltage $V_{OLM}$ from the limiter circuit 105 when the limiter circuit 105 is not operating has a characteristic shown by $$V_{OLM} = V_0 = [\{K \times \eta \times (1+G_1) \times G_2\}/(1+K \times \eta \times G_1 \times G_2)] \times V_1$$
(expression 4), where it is to be understood that $K = G_3 \times G_4 \times G_5 \times G_6$.

In the above-mentioned expression 4, K, $G_1$ and $G_2$ are constants and thus, the output voltage $V_0$ from the amplifying circuit 100 is determined by the light quantity transmissibility $\eta$ and the reference voltage $V_1$. Also, when the output voltage $V_0$ of the amplifying circuit 100 reaches the upper limit value of the limiter circuit 105, it is limited to $V_{OLM} = V_H$ which is the upper limit voltage of the limiter circuit 105. Also, when the output voltage $V_0$ reaches the lower limit value of the limiter circuit 105, it is limited to $V_{OLM} = V_L$ which is the lower limit voltage of the limiter circuit 105.

Also, when a current for driving the light emitter 60 is defined as $J_1$, the input light quantity i2 to the light receiver 80 becomes $$i2 = J_1 \times G_3 \times \eta \quad \text{(expression 5)}.$$

From the above-mentioned expression 3, expression 4 and expression 5, the current $J_1$ for driving the light emitter 60 has a characteristic shown by $$J_1 = [(1+G_1) \times G_2/(1+K \times \eta \times G_1 \times G_2)] \times V_1 \quad \text{(expression 6)}.$$

Figure 5:
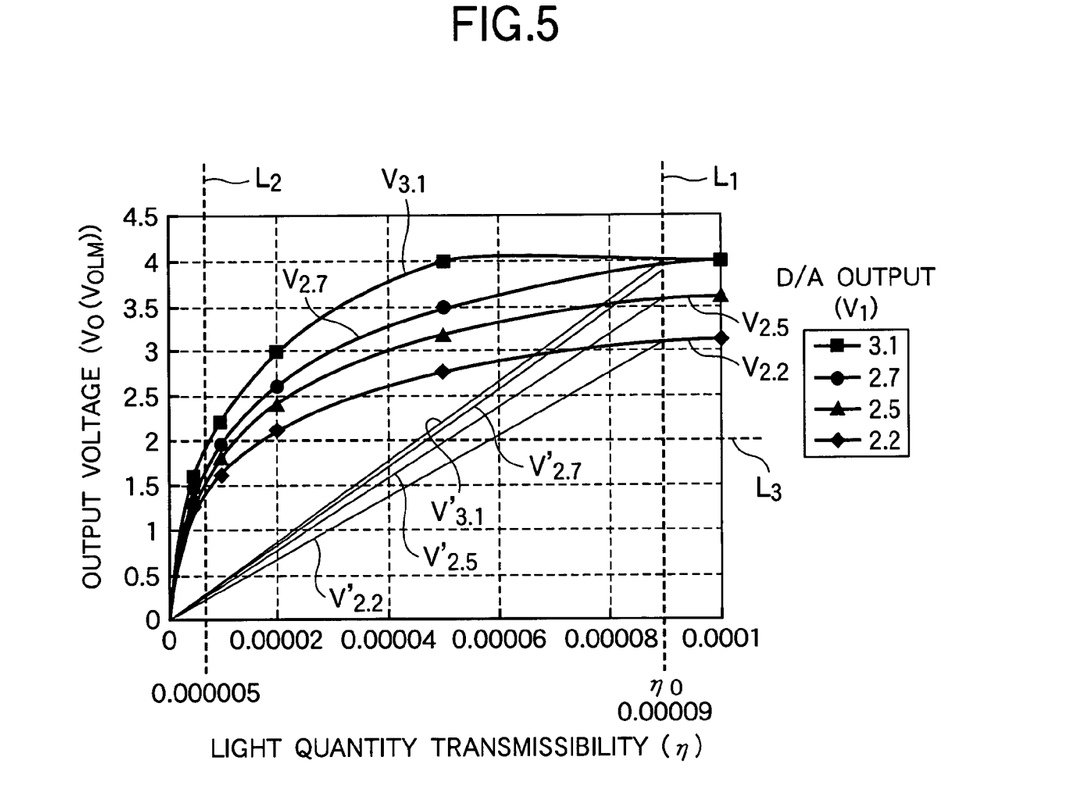
FIG. 5 is a characteristic graph of the sheet detecting apparatus according to the present embodiment.

The characteristics of the light quantity transmissibility $\eta$ from the light emitter 60 to the light receiver 80 and the output voltage $V_0$ from the limiter circuit 105 shown in the above-mentioned expression 4 are shown in the characteristic graph of FIG. 5. In FIG. 5, $V_{3.1}$, $V_{2.7}$, $V_{2.5}$ and $V_{2.2}$ indicate the characteristic graphs when the reference voltage $V_1$ is 3.1V, 2.7V, 2.5V and 2.2V, respectively. Also, in FIG. 5, $V'_{3.1}$, $V'_{2.7}$, $V'_{2.5}$ and $V'2.2$ indicate the characteristic graphs of the output voltage $V_{OLM}$ from the limiter circuit 105 when not provided with the comparing circuit 120 with respect to cases where the output voltage $V_1$ from the D/A converter 20 is 3.1V, 2.7V, 2.5V and 2.2V, respectively. Also, in FIG. 5, the upper limit voltage of the limiter circuit 105 is $V_H = V_{OLM} = 4.0V$, and the lower limit voltage of the limiter circuit 105 is $V_L = V_{OLM} = 0.7V$.

In FIG. 5, the broken line $L_1$ indicates the light quantity transmissibility when the sensor portion S is not light-intercepted by the sheet conveyed to the conveying path 130, and the light quantity transmissibility at this time is $\eta \approx 0.00009$. In FIG. 5, the light quantity transmissibility indicated by broken line $L_1$ indicates initial light quantity transmissibility $\eta 0$ for which the sensitivity is not lowered by paper powder or the like.

In FIG. 5, the broken line $L_2$ indicates the light quantity transmissibility when the sheet conveyed to the conveying path 130 is thin paper and the sensor portion S is light-intercepted by this sheet, and the light quantity transmissibility at this time is $\eta \approx 0.000005$.

Also, in FIG. 5, the broken line $L_3$ indicates a threshold value when the sensor portion S judges the presence or absence of the sheet, and in the present embodiment, it is set to 2.0V which is ½ of the upper limit voltage $V_{OLM} = 4.0V$ of the limiter circuit 105. The threshold value is a value which can be arbitrarily set.

Accordingly, according to the characteristic graph shown in FIG. 5, the sensor portion S is lowered in sensitivity by paper powder or the like and the light quantity transmissibility is lowered, and the light quantity transmissibility when the output voltage $V_0$ from the limiter circuit 105 has coincided with a threshold value $L_3$ is defined as $\eta$th, and the value of $\eta$th becomes small as compared with the value of light quantity transmissibility $\eta$th' when output voltages $V'_{3.1}$, $V'_{2.7}$, $V'_{2.5}$ and $V'_{2.2}$ from the limiter circuit 105 when not provided with the comparing circuit 120 and the threshold value $L_3$ coincide with each other. From this, it is seen that the sheet detecting apparatus according to the present embodiment is great in the margin which can measure the presence or absence of the sheet even if the sensitivity of the sensor portion S is lowered.

Figure 6:
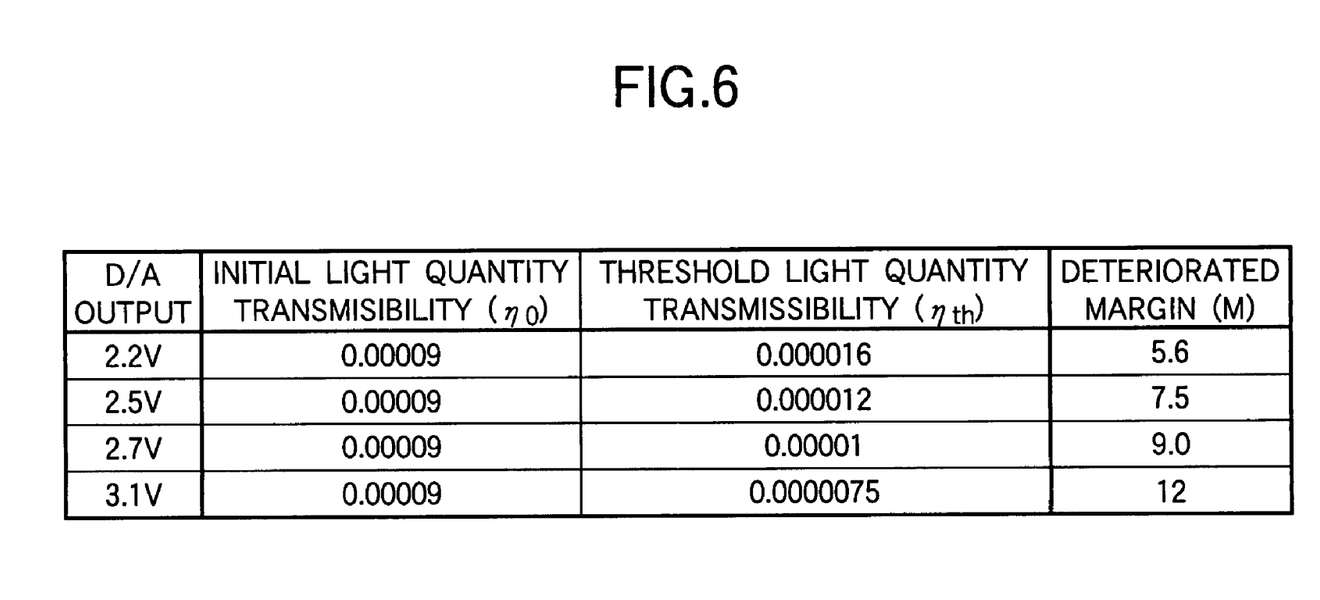
FIG. 6 is a table showing the deteriorated margin of the sheet detecting apparatus according to the present embodiment.

FIG. 6 shows the deteriorated margin $M = \eta 0/\eta$th at which the sensor portion S can detect the presence or absence of the sheet when the threshold value is 2.0V and the output voltage $V_1$ from the D/A converter 20 is 3.1V, 2.7V, 2.5V and 2.2V.

From FIG. 6, it is seen that when for example, the output voltage from the D/A converter 20 is 2.7V, the deteriorated margin M is 9.0, and this shows that the sensor portion S can detect the presence or absence of the sheet even if the light quantity transmissibility q from the light emitter 60 to the light receiver 80 becomes ⅑ by dust or the like adhering, for example, to the light emitter 60.

The output voltage $V_1$ from the D/A converter 20 can be arbitrarily set, but if the value of $V_1$ is too great, as is apparent from the above-mentioned expression 6, the current $J_1$ passing through the light emitter 60 will become too great, thus resulting in the shortening of the life of the LED which is the light emitter 60. Accordingly, it is necessary to determine the output voltage $V_1$ from the D/A converter 20 with the allowable current of the light emitter 60 taken into account.

Also, when the sensor portion S is light-intercepted by the sheet conveyed to the conveying path 130, the incident light quantity i2 onto the light receiver 80 infinitely approximates to zero and therefore, $\eta \approx 0$, and from the above-mentioned expression 6, the current $J_1$ for driving the light emitter 60 assumes a maximum value $J_{1max}$ represented below by expression 7.

$$J_{1max} = (1+G_1) \times G_2 \times V_1 \quad \text{(expression 7)}$$

Therefore, it is necessary to determine the output voltage $V_1$ from the D/A converter 20 so as to satisfy the upper limit of the driving current for the light emitter 60.

Accordingly, the output voltage $V_1$ from the D/A converter 20 is optimized and determined with the allowable current or the upper limit value of the driving current for the light emitter 60 taken into account while the CPU 200 monitors the output voltage $V_{OLM}$ from the limiter circuit 105.

If as described above, the output voltage $V_1$ from the D/A converter 20 is set to an optimum value during the initial setting, thereafter the comparing circuit 120 works so as to maintain the light quantity transmissibility $\eta$ of the sensor portion S and therefore, periodical sensor adjustment becomes unnecessary.

Figure 7:
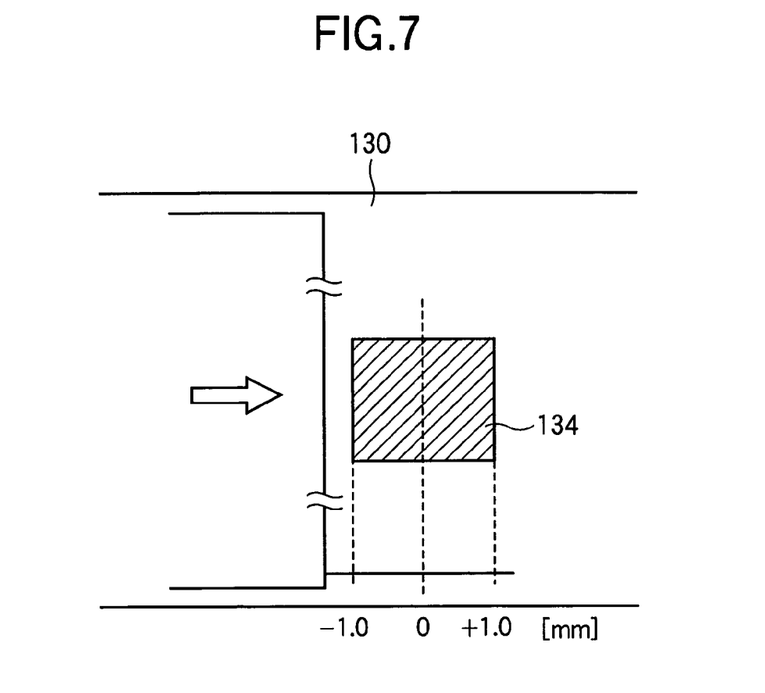
FIG. 7 is a plan view showing a state in which the leading edge of a sheet passes on a slit.

FIG. 7 is a plan view showing a state in which the leading edge of the sheet passes on the second slit 134 provided in one conveying guide 132 of the conveying path 130 shown in FIG. 3. In the sheet detecting apparatus according to the present embodiment, the second slit 134 is a rectangle of which one side is 2 mm. In FIG. 7, the front and rear sides of the second slit 134 in the sheet conveying direction are −1 mm and +1 mm, respectively, and the coordinates are determined with the center of the two sides as the zero point.

Figure 8:
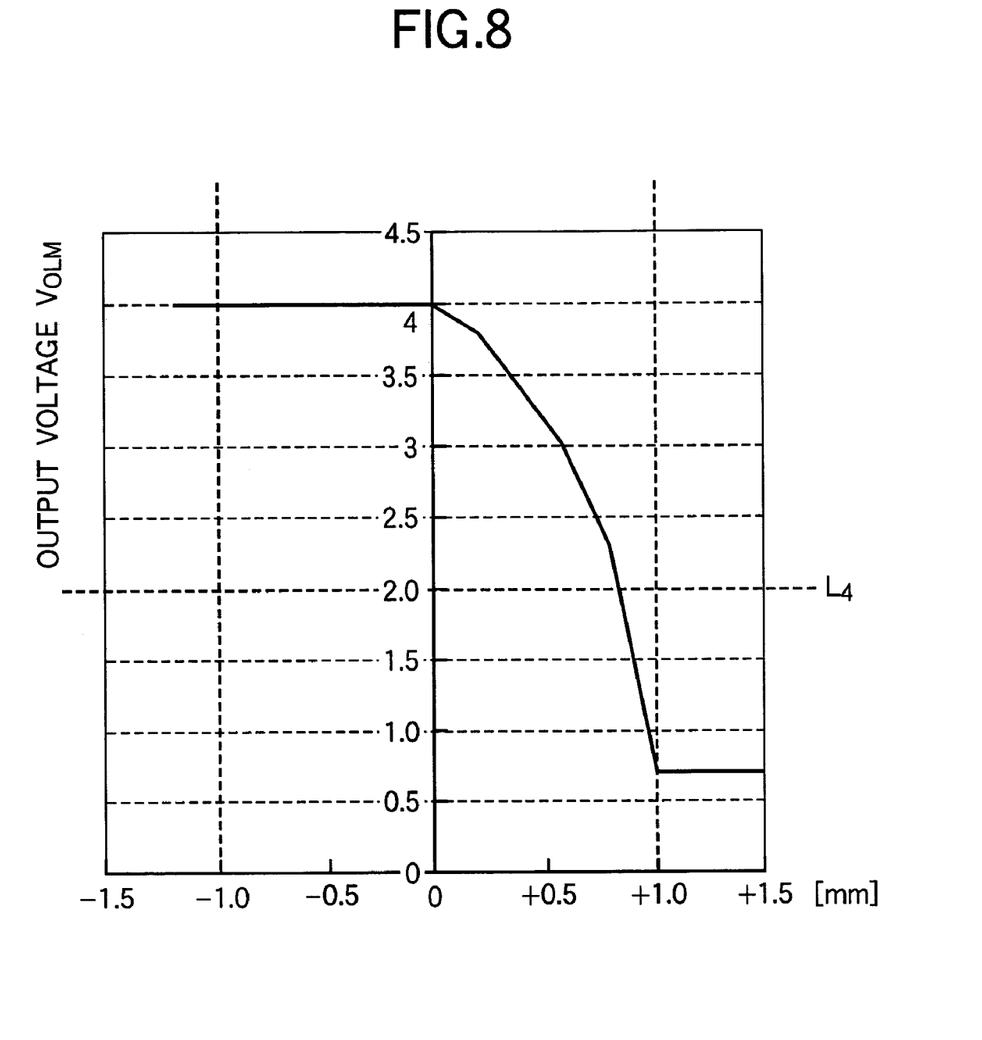
FIG. 8 is a characteristic graph showing the characteristic of an output voltage $V_{OLM}$ when the leading edge of the sheet passes on the slit.

FIG. 8 is a characteristic graph showing the output voltage $V_{OLM}$ of the limiter circuit 105 when the leading edge of the sheet passes on the second slit 134 shown in FIG. 7. In FIG. 8, the axis of abscissas corresponds to the coordinates of the second slit 134 shown in FIG. 7 in the sheet conveying direction. Also, the axis of ordinates corresponds to the output voltage $V_{OLM}$ from the limiter circuit 105. That is, it shows the output characteristic of the output voltage $V_{OLM}$ from the limiter circuit 105 when the leading edge of the sheet moves on the second slit 134 from the left position of −1 mm to the position of +1 mm in FIG. 7.

In FIG. 8, the broken line $L_4$ indicates a threshold value when the sensor portion S judges the presence or absence of the sheet, and in the present embodiment, it is set to 2.0V which is ½ of the upper limit voltage $V_{OLM}$=4.0V of the limiter circuit 105.

As is apparent from FIG. 8, the sheet detecting apparatus according to the present embodiment is provided with the comparing circuit 120 and the limiter circuit 105 and therefore, in the second slit 134, the position at which the sensor portion S judges the presence or absence of the sheet is judged when the leading edge of the sheet has arrived at the vicinity of the downstream side (+1 mm side) of the slit 134 with respect to the conveying direction.

Accordingly, even if the width of the second slit 134 in a direction perpendicular to the conveying direction is made great, the sheet detecting position can be near the downstream side end of the second slit 134 with respect to the conveying direction and therefore, it becomes possible to always enhance the detection accuracy of the sheet without being affected by the disposition of the sensor portion S and the conveyed state of the sheet. Accordingly, as compared with the conventional sheet detecting apparatus in which it has been necessary to narrow the slit width in order to enhance the detection accuracy of the sheet, the slit width can be widened and the problem of the wrong detection of the sheet occurring from the slight deviation of the optical axis linking the light emitter 60 and the light receiver 80 together can also be solved.

As described above, in the sheet detecting apparatus according to the present embodiment, the quantity of emitted light of the light emitter 60 can be automatically corrected so that the quantity of light from the light receiver 80 may become optimum for detecting the sheet passing on the conveying path 130, to thereby prevent wrong detection. Further, the automatic correction can be made to follow even such an unexpected cause as a sudden change in temperature or the temporary adherence of dust to thereby effect detection appropriately and prevent wrong detection.

This application claims priority from Japanese Patent Application No. 2003-416623 filed Dec. 15, 2003, which is hereby incorporated by reference herein.

What is claimed is:

1. A sheet detecting apparatus comprising:
    a sheet feeding device;
    a light emitter;
    a light receiver for receiving light emitted from said light emitter through a sheet conveying path downstream of said sheet feeding device;
    a driver for driving said light emitter;
    a comparing circuit for effecting negative feedback on said driver by an output signal from said light receiver, and changing the quantity of light of said light emitter;
    a limiter for applying a limitation to an amount of feedback from said comparing circuit effected on said driver by said comparing circuit; and
    a control circuit for discriminating a presence or absence of a sheet on said sheet conveying path in accordance with an output signal of said limiter.

2. A sheet detecting apparatus according to claim 1, wherein said comparing circuit effects the negative feedback on said driver so that the quantity of light from said light emitter received by said light receiver when the sheet is not passing on the sheet conveying path may maintain an allowable quantity of received light.

3. A sheet detecting apparatus according to claim 1, wherein an optical path from said light emitter to said light receiver is astride said sheet conveying path at a plurality of locations.

4. A sheet detecting apparatus according to claim 1, wherein said light emitter and said light receiver are disposed on one sheet surface side of said sheet conveying path, and a light guiding member for guiding the light from said light emitter to said light receiver is disposed on the other sheet surface side of said sheet conveying path.

5. A sheet detecting apparatus according to claim 4, wherein said light guiding member is a prism.

6. A sheet detecting apparatus according to claim 1, wherein said light emitter and said light receiver are disposed side by side in a direction orthogonal to a sheet conveying direction.

7. A sheet detecting apparatus according to claim 1, wherein said limiter applies a limitation to both of an upper limit and a lower limit of the amount of feedback to said driver.

* * * * *

UNITED STATES PATENT AND TRADEMARK OFFICE
CERTIFICATE OF CORRECTION

PATENT NO. : 7,401,779 B2  
APPLICATION NO. : 11/001040  
DATED : July 22, 2008  
INVENTOR(S) : Sekiya et al.

It is certified that error appears in the above-identified patent and that said Letters Patent is hereby corrected as shown below:

IN THE DRAWINGS:
Sheet No. 5, Figure 6, "TRANSMISIBILITY" should read --TRANSMISSIBILITY--.

COLUMN 2:
Line 29, "such a" should read --such as a--.
Line 39, "being about" should read --bring about--.

COLUMN 3:
Line 31, "back diagram" should read --block diagram--.

COLUMN 4:
Line 20, "silt 133" should read --slit 133--.
Line 47, "compring" should read --comparing--.

COLUMN 6:
Line 12, "V'2.2" should read --$V'_{2.2}$--.
Line 59, "transmissibility q" should read --transmissibility η--.

Signed and Sealed this

Thirteenth Day of January, 2009

JON W. DUDAS  
*Director of the United States Patent and Trademark Office*